(12) United States Patent
Vardi et al.

(10) Patent No.: US 6,659,957 B1
(45) Date of Patent: Dec. 9, 2003

(54) OPTICAL-ACOUSTIC IMAGING DEVICE

(76) Inventors: Gil M. Vardi, 14203 Stifel Lane Ct., Town & Country, MO (US) 63017; Victor Spivak, deceased, late of Kiriat Bialik (IL); by Evgeni Spivak, administrator, Charlotten Str. #24, 13597 Berlin (DE)

( * ) Notice: Subject to any disclaimer, the term of this patent is extended or adjusted under 35 U.S.C. 154(b) by 0 days.

(21) Appl. No.: 09/623,248

(22) PCT Filed: Mar. 5, 1999

(86) PCT No.: PCT/US99/04913
§ 371 (c)(1),
(2), (4) Date: Jun. 11, 2002

(87) PCT Pub. No.: WO99/58059
PCT Pub. Date: Nov. 18, 1999

Related U.S. Application Data

(60) Provisional application No. 60/076,862, filed on Mar. 5, 1998.

(51) Int. Cl.[7] ............................................. A61B 8/14
(52) U.S. Cl. ........................................................ 600/467
(58) Field of Search ................................ 600/407–471, 600/477, 129, 160; 356/450, 477, 479; 73/625, 626; 367/7, 11, 153, 157, 173, 174, 180; 385/12; 606/15; 359/278, 279, 287

(56) References Cited

U.S. PATENT DOCUMENTS

| | | | |
|---|---|---|---|
| 5,095,911 A | 3/1992 | Pomeranz | 128/662.06 |
| 5,186,177 A | 2/1993 | O'Donnell | 128/662.06 |
| 5,226,847 A | 7/1993 | Thomas, III et al. | 128/662.06 |
| 5,240,004 A | 8/1993 | Walinsky et al. | 128/662.06 |
| 5,290,275 A | * 3/1994 | Kittrell et al. | 606/15 |

(List continued on next page.)

FOREIGN PATENT DOCUMENTS

WO WO-01/21244 3/2001 .......... A61M/25/10

OTHER PUBLICATIONS

Blotekjaer, K., "Theoretical concepts of a novel Vernier-–based fringe–counting fibre optic sensor", *IEEE Proceedings, Optoelectronics, 144, 3*, (Jun. 1997), 126–129.

Brady, G. P., et al., "Simultaneous measurement of strain and temperature using the first–and second–order diffraction wavelengths of Bragg gratings", *IEEE Proceedings, Optoelectronics, 144, 3*, (Jun. 1997), 156–161.

Davis, M. A., et al., "Simultaneous measurement of temperature and strain using fibre Bragg gratings and Brillouin scattering", *IEE Proceedings, Optoelectronics, 144, 3*, (Jun. 1997), 151–155.

(List continued on next page.)

*Primary Examiner*—Marvin M. Lateef
*Assistant Examiner*—Ali M. Imam
(74) *Attorney, Agent, or Firm*—Schwegman, Lundberg, Woessner & Kluth, P.A.

(57) ABSTRACT

The present invention is a guide wire imaging device for vascular or non-vascular imaging utilizing optic acoustical methods, which device has a profile of less than 1 mm in diameter. The ultrasound imaging device of the invention comprises a single mode optical fiber with at least one Bragg grating (8), and a piezoelectric or piezo-ceramic jacket (31), which device may achieve omnidirectional (360°) imaging. The imaging guide wire of the invention can function as the guide wire for vascular interventions, can enable real time imaging during balloon inflation, and stent deployment, thus will provide clinical information that is not available when catheter based imaging systems are used. The device of the invention may enable shortened total procedure times, including the fluoroscopy time, will also reduce radiation exposure to the patient, and the operator.

16 Claims, 5 Drawing Sheets

U.S. PATENT DOCUMENTS

| | | | | |
|---|---|---|---|---|
| 5,305,758 A | * | 4/1994 | Dietz et al. | 600/465 |
| 5,383,467 A | * | 1/1995 | Auer et al. | 600/342 |
| 5,400,788 A | | 3/1995 | Dias et al. | 128/662.03 |
| 5,427,107 A | | 6/1995 | Milo et al. | 128/662.06 |
| 5,439,000 A | * | 8/1995 | Gunderson et al. | 600/473 |
| 5,582,171 A | | 12/1996 | Chornenky et al. | 128/653.1 |
| 5,601,087 A | | 2/1997 | Gunderson et al. | 128/664 |
| 5,660,180 A | | 8/1997 | Malinowski et al. | 128/660.03 |
| 5,675,674 A | * | 10/1997 | Weis | 385/12 |
| 5,682,897 A | | 11/1997 | Pomeranz | 128/662.06 |
| 5,779,643 A | | 7/1998 | Lum et al. | 600/462 |
| 5,852,233 A | | 12/1998 | Arnold et al. | 73/105 |
| 5,865,178 A | | 2/1999 | Yock | 128/660.03 |
| 5,872,879 A | | 2/1999 | Hamm | 385/25 |
| 5,894,531 A | | 4/1999 | Alcoz | 385/11 |
| 5,938,609 A | | 8/1999 | Pomeranz | 600/439 |
| 6,039,701 A | * | 3/2000 | Sliwa et al. | 600/588 |
| 6,057,927 A | | 5/2000 | Levesque et al. | 356/432 T |
| 6,078,831 A | | 6/2000 | Belef et al. | 600/424 |
| 6,111,645 A | * | 8/2000 | Tearney et al. | 356/499 |
| 6,228,078 B1 | | 5/2001 | Eggers et al. | 606/32 |
| 6,238,347 B1 | | 5/2001 | Nix et al. | 600/463 |
| 6,248,076 B1 | | 6/2001 | White et al. | 600/463 |
| 6,261,246 B1 | | 7/2001 | Pantages et al. | 600/585 |
| 6,282,011 B1 | * | 8/2001 | Tearney et al. | 359/287 |
| 6,306,096 B1 | | 10/2001 | Seward et al. | 600/463 |
| 6,421,164 B2 | * | 7/2002 | Tearney et al. | 359/287 |

OTHER PUBLICATIONS

Feced, R., et al., "Advances in high resolution distributed temperature sensing using the time–correlated single photon counting technique", *IEEE Proceedings, Optoelectronics, 144, 3*, (Jun. 1997), 183–188.

Furstenau, N., et al., "Extrinsic Fabry–Perot interferometer vibration and accoustic sensor systems for airport ground traffic monitoring", *IEE Proceedings, Optoelectronics, 144, 3*, (Jun. 1997), 134–144.

Lockey, R. A., "Multicomponent time–division–multiplexed optical fibre laser Doppler anemometry", *IEE Proceedings, Optoelectronics, 144, 3*, (Jun. 1997), 168–175.

Macpherson, W. N., et al., "Phase demodulation in optical fibre Fabry–Perot sensors with inexact phase steps", *IEE Proceedings, Optoelectronics, 144, 3*, (Jun. 1997), 130–133.

McCulloch, S., et al., "Development of a fibre optic micro–optrode for intracellular pH measurements", *IEE Proceedings, Optoelectronics, 144, 3*, (Jun. 1997), 162–167.

Tanaka, S., et al., "Fibre optic spectral polarimetry for sensing multiple stress–loaded locations along a length of fibre", *IEE Proceedings, Optoelectronics, 144, 3*, (Jun. 1997), 176–182.

Yoshino, T., et al., "Spiral fibre microbend sensors", *IEE Proceedings, Optoelectronics, 144, 3*, (Jun. 1997), 145–150.

* cited by examiner

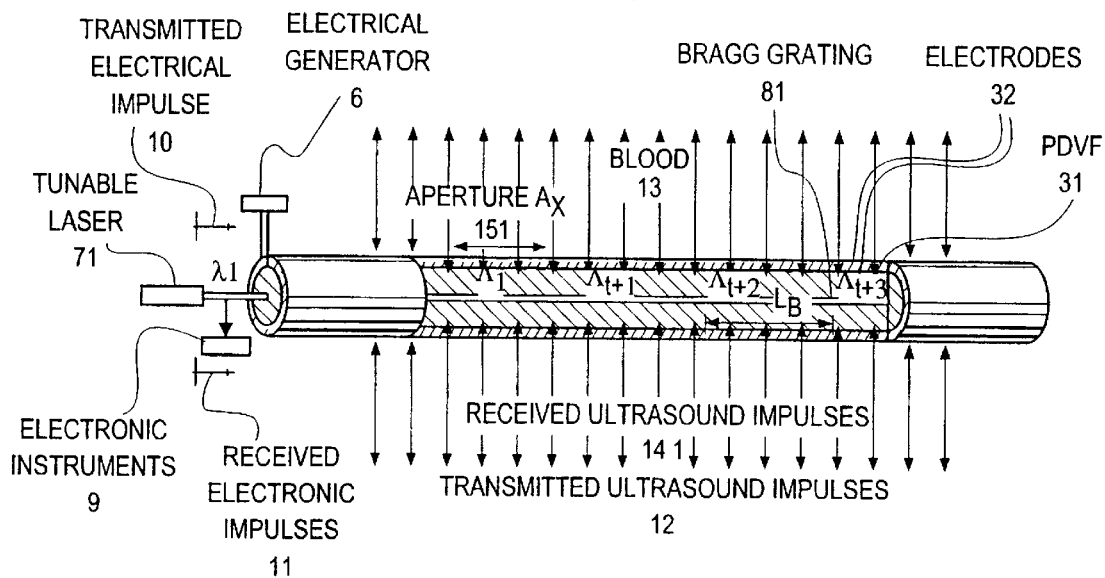
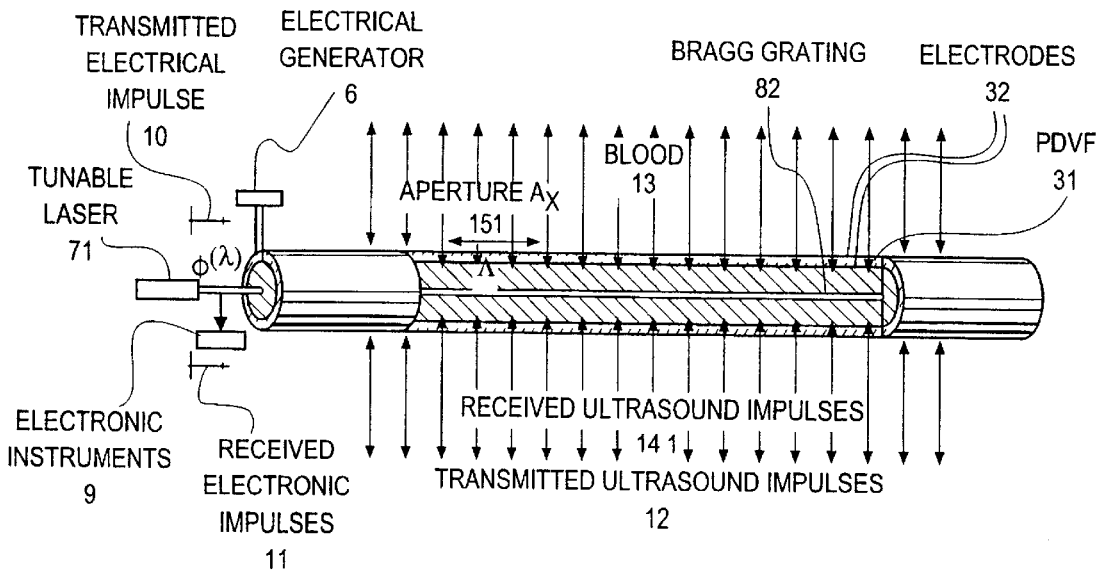

STRENGTH MEMBER
52

FILLER 16  SILICA BEADS 21  ELECTRODES 32  PVDF 31

BRAGG GRATING 81  $L_C$

SILICA BEADS 22

RIBS 23  $T_r$

STRENGTH MEMBER 51  LENSE 17

OPTICAL-ACOUSTIC IMAGING DEVICE

RELATED APPLICATIONS

This application claims priority to U.S. Provisional Application No. 60/076,862, filed on Mar. 5, 1998.

FIELD OF THE INVENTION

The present invention relates to an omnidirectional imaging device for vascular or nonvascular imaging that may be used as an intravascular guidewire.

BACKGROUND OF THE INVENTION

Intra-vascular and non-vascular imaging are very important techniques that provides information that is not available by angiographic imaging methods such as information about the composition of the subject vessel wall, plaque analysis, and disease processes. It is also very important as an aid to vascular interventions, especially stent deployment.

Prior art intra-vascular ultrasound (IVUS) devices are described as generally adapted to be used via catheter, and are primarily either mechanical or solid state. In the mechanical IVUS catheter, image scanning is accomplished by a rotating drive shaft causing mechanical rotation of a miniature acoustical transmitter. The drive shaft and most of the transmitter are located within the body of a flexible catheter. The design of these devices generally creates difficulties in tracking with a limited image area, and vibration of the catheter during rotation poses a risk to the patient of arterial spasm.

The solid state IVUS catheter does not have a rotating driveshaft, but rather produces images by scanning with electrical impulses that are generated from a large number of piezoelectric elements located within the IVUS. Each piezoelectric element is controlled by a driver such as a computer. Conventional solid state IVUS devices generally have a lumen adapted to receive a guidewire, and a coaxial cable design which enhances the trackability and pushability of the device as compared to the mechanical model.

One deficiency in conventional mechanical and solid state IVUS catheters is the external diameter, generally approximately 1.2 mm. Mechanical limitations on component sizes and noise effects have thus far limited commercially feasible manufacture of a smaller diameter device. In addition, both these devices must be used with traditional intraluminal catherization methods, that is, with the catheter situated over a guidewire.

Some prior art ultrasonic catheter patents describe a thin films of a flexible piezoelectric plastic material, such as poled polyvinyldiene fluoride (PVDF), which can be spot polarized in active regions to serve as piezoelectric transducers. In these devices, the PVDF film is used both as a transmitter and as a receiver. However, it is difficult to adapt this technology to small (less than 1.2 mm diameter) imaging catheters with multiple elements, for several reasons. One such reason is the very low electrical capacitor of each of the receiver elements having a small surface area as compared to the capacitor of the long electrode conductors (more then 1 m long). This relationship of elements in the device generally results in a low signal/noise relation. While the signal to noise ration may be increased by the use of preamplifiers near the receivers, physically accommodating the preamplifiers inside of a space with an outer diameter of less than 1.2 mm is very difficult. Another reason is the large signal cross talk experienced due to the long, closely clustered conductors within the device.

Other relevant prior art technology that couples ultrasonic waves with an optical fiber in an intravascular device includes a transducer which is precisely located on thin slab of piezoelectric material. The transducer generates ultrasonic acoustic surface waves that propagate on the surface or within the bulk of the slab. These devices are limited, however, in that they generate doppler signals and not images, and their probing range is limited to the area just in front of the catheter pass. Also, the piezoelectric chip is not small enough to be used in a device with a profile diameter of less than 1 mm and more importantly, less than 0.5 mm.

In most commercially available piezoceramic and PVDF IVUS devices, one significant problem is the difficulty in constructing ultrasound imaging catheters with a diameter of less then approx. 1 mm., and where the signal to noise ratio will be high enough for the device to be easily used. Such devices are also difficult to manufacture from a mechanical perspective, using conventional components.

Accordingly, it would be useful to have an intra-vascular ultrasound imaging device with a profile of less that approximately 1 mm in diameter and most preferably less than 0.5 mm in diameter, with a signal/noise ratio that is higher than those generated by conventional IVUS devices such as those described above. It would also be useful to have an imaging device for non-vascular applications which demand a device profile of less than I mm.

SUMMARY OF THE INVENTION

The present invention is a guidewire imaging device for vascular or non-vascular imaging utilizing optico-acoustical methods, which device has a profile of less than 1 mm in diameter, and most preferably less than 0.5 mm in diameter. The imaging device of the invention comprises a single-mode optical fiber with at least one Bragg grating and a piezoelectric or piezoceramic jacket, which device may achieve omnidirectional (360°) imaging. The imaging guidewire of the invention can function as the guidewire for vascular interventions, and can enables real time imaging during balloon inflation and stent deployment, thus will provide clinical information that is not available when catheter-based imaging systems are used. The device of the invention may enable shortened total procedure times, including the fluoroscopy time, and will also reduce radiation exposure to the patient and the operator.

Thus, it is an object of the invention to provide an optico-acoustic device for vascular or non-vascular imaging with a profile of less than 1 mm, and most preferably less than 0.5 mm.

Another object of the invention is to provide a guidewire imaging device for producing real time images during vascular intervention procedures prior to catheter insertion and throughout the procedure.

A further object of the invention is to provide a device which is capable of omnidirectional 360 degree imaging.

Still another object of the invention is to provide an intravascular imaging technique with an improved signal to noise ratio over prior art intravascular imaging devices.

DESCRIPTION OF THE FIGURES

FIG. 5 is a schematic diagram of a PVDF and FBG based ultrasound pulser-receiver having a plurality of Bragg gratings.

FIG. 6 is a schematic diagram of a PVDF and FBG based ultrasound pulser-receiver having a plurality of variable Bragg gratings.

DESCRIPTION OF THE PREFERRED EMBODIMENTS

Figure 1:
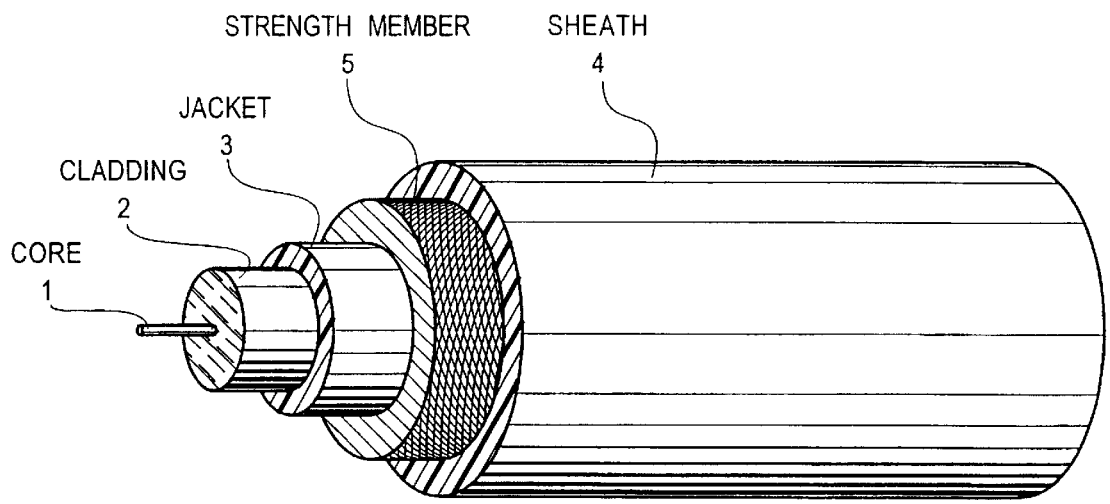
FIG. 1 is a schematic diagram of a conventional optical fiber.
Figure 2:
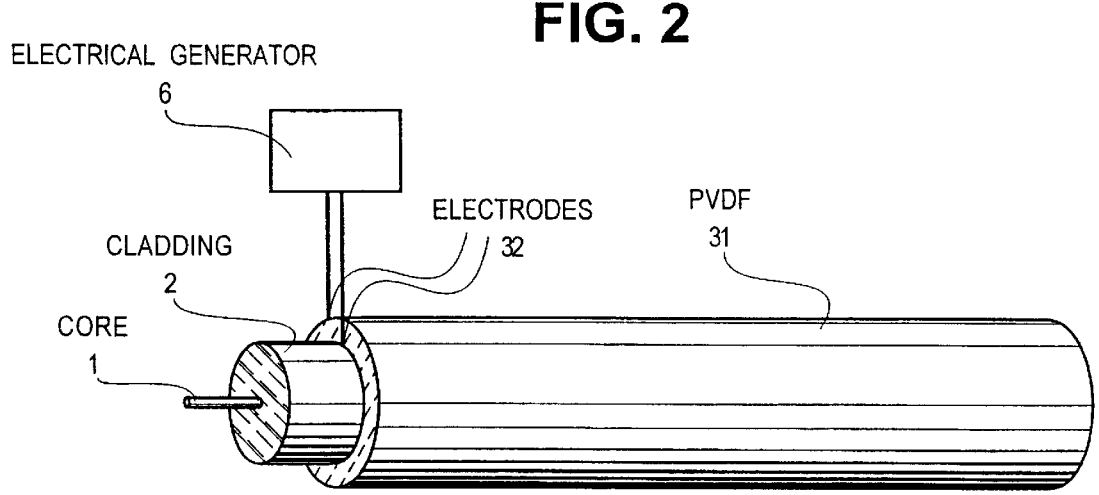
FIG. 2 is schematic diagram of a PVDF jacketed optical fiber.

The device of the invention utilizes a single optical fiber, for example but not limited to a glass fiber at least partly composed of silicon dioxide. The basic structure of a generic is optical fiber is illustrated in FIG. 2, which fiber generally consists of layered glass cylinders. There is a central cylinder called the core 1. Surrounding this is a cylindrical shell of glass, possibly multilayered, called the cladding 2. This cylinder is surrounded by some form of protective jacket 3, usually of plastic (such as acrylate). For protection from the environment and more mechanical strength than jackets alone provide, fibers are commonly incorporated into cables. Typical cables have a polyethylene sheath 4 that encases the fibers within a strength member 5 such as steel or Kevlar strands.

Optical fibers can be broadly classified according to their refractive index profile and dimensions. The invention described below uses single-mode fibers.

FIG. 2 shows an optical fiber coated by a piezoelectric jacket, to which an alternating voltage electrical generator 6 is attached to electrodes 32 situated on either side of the jacket. the generator 6 sends electrical impulses to the electrodes 32, which impulses cause mechanical oscillations in the jacket 31.

In recent years Fiber Bragg Grating (FBG) sensors have generated great interest because of their potential use in a wide range of applications such as telecommunications. FBGs form an integral part of the optical fiber structure and can be written intracore during manufacture or after manufacture.

Figure 3:
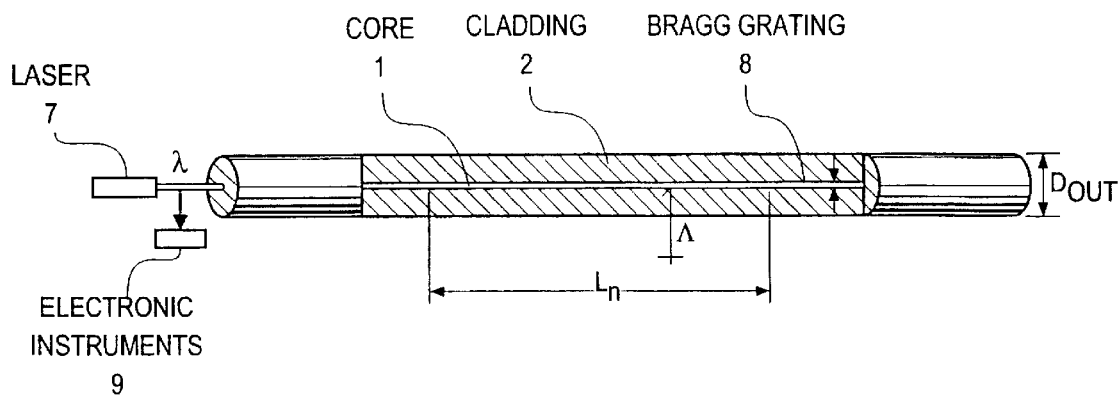
FIG. 3 is a schematic diagram of a Fiber Bragg Grating based sensor.

As illustrated in FIG. 3, when illuminated by a broadband light laser 7, a uniform pitch Fiber Bragg Grating ("FBG") element 8 will reflect back a narrowband component centered about the Bragg wavelength $\lambda$ given by $\lambda=2n\Lambda$, where n is the index of the core of the fiber and $\Lambda$ represents the grating period. Using a tunable laser 7 and different grating periods (each period is approximately $0.5\mu$) situated in different positions on the fiber, it is possible to make independent measurement in each of the grating positions.

EXAMPLE 1

Figure 4:
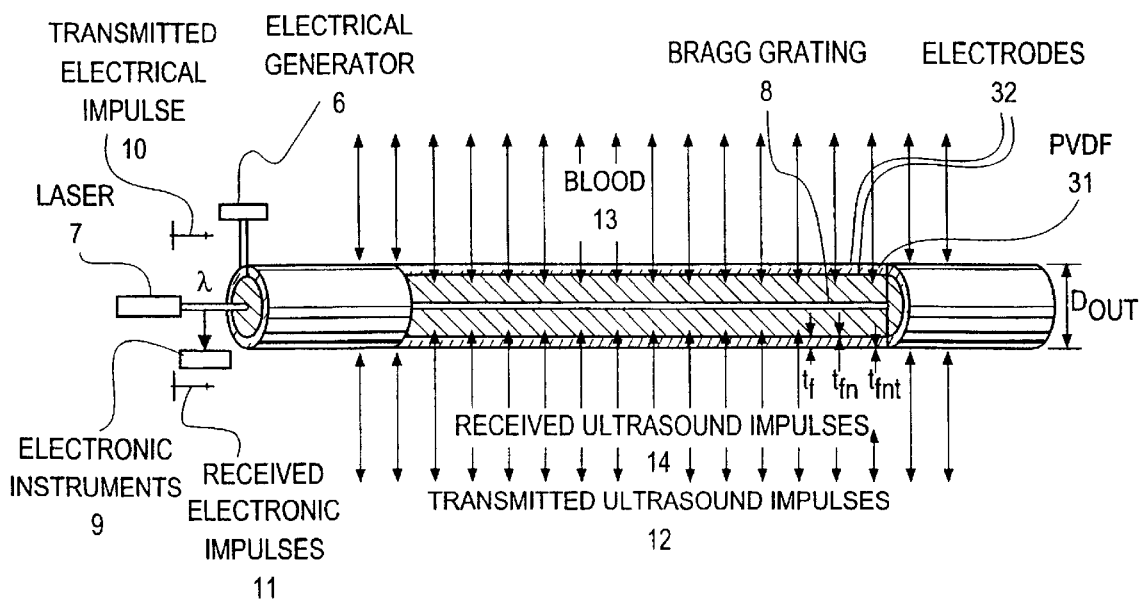
FIG. 4 is a schematic depiction of a PVDF and FBG based ultrasound pulser-receiver of the invention.

One preferred embodiment of the invention is illustrated in FIG. 4. This embodiment includes a single-mode optical fiber with a Bragg grating 8 and a piezoelectric or piezoceramic jacket 31. The jacket may be any suitable piezoelectric or piezoceramic material, and one preferable material is poled PVDF. It is contemplated that other jacket materials will work with the invention, so long as the material has suitable flexibility and piezoelectric characteristics.

In the preferred embodiment of the device of the invention as illustrated in FIG. 4, an electrical generator 6 transmits ultrasound impulses 10 to both the Bragg grating 8 and to the outer medium 13 in which the device is located, for example, the blood. Primary and reflected impulses 11 are received by the Bragg grating 8 and recorded by electronic instruments 9 using conventional methods, such as by a photodetector and an oscilloscope. From the recorded signals, a corresponding image is generated by conventional methods. Hence, the invention utilizes omnidirectional sonar (pulser-receiver) at each of the imaging locations. If mechanical deformations appear inside the optical fiber, they cause modulation of light reflected backward, which is received by the electronic instruments 9.

It is contemplated that in the various devices constructed according to the invention, the thickness of the jacket as well as the diameter of the optical fiber may vary significantly, and the only requirement is that the entire device be less than 1 mm and most preferably less than $300\mu$, and that the signals generated by the device are suitable to generate an image.

The ultrasound transmitter device of the invention comprises a single fiber covered by a piezoelectric active (poled) PVDF jacket has a total outside diameter of preferably less than 1 mm, and most preferably less than $300\mu$. It is also contemplated that devices may be made in accordance with the principles of the invention with profiles of approximately or less than $200\mu$. Devices with other frequency transmitters may also be constructed in accordance with the principles of the invention, as applications dictate. The device of the invention includes any needed frequency of transmitter.

EXAMPLE 2

It may also be possible to expand the frequency band of the signal by using a damped silica fiber. In this variation of the preferred embodiment of the invention, frequency band expansion causes shortening of the signal in time, which improves the resolution of the received signal. For instance, using a damped fiber in a device of the invention, we have obtained maximum widths of the frequency band of the signal of approximately 110, although another variations will be achieved depending upon experimental conditions. If damped fibers are utilized, transmitters transmitting at less than 40 MHz may be used.

EXAMPLE 3

As shown in FIG. 5, one other preferred embodiment of an imaging device in accordance with the invention comprises a plurality of Bragg gratings 81 with different periods, each period being approximately $0.5\mu$. By using multiple Bragg gratings, a set of distributed sonars are obtained. By utilizing a tunable laser 71 as previously described, we obtain scanning over an omnidirectional array. A Bragg grating length $L_B$ of some hundreds of optical wavelengths are sufficient to reflect considerable part of the optical beam. The ultrasound impulses 141 are received only by the Bragg gratings 81, with the period of $\Lambda_i$ which is equal to the aperture $A_x$.

EXAMPLE 4

In yet another preferred embodiment of a device of the invention as illustrated in FIG. 6, instead of a plurality of Bragg gratings, the device may incorporate a single variable grating, with a variable period. When a tunable laser is adjusted to the wavelength $\lambda_1$ the receiving element is the Bragg grating. When the laser wavelength is adjusted to other wavelengths $\lambda_{2-6...}$, the corresponding positioning of the Bragg grating along the axis of the fiber is also adjusted.

We have determined that for a device with a 40 MHz frequency transmitter and aperture $A_x=151-200\mu$, the reception obtained by the invention provides acceptable imaging.

EXAMPLE 5

Figure 7:
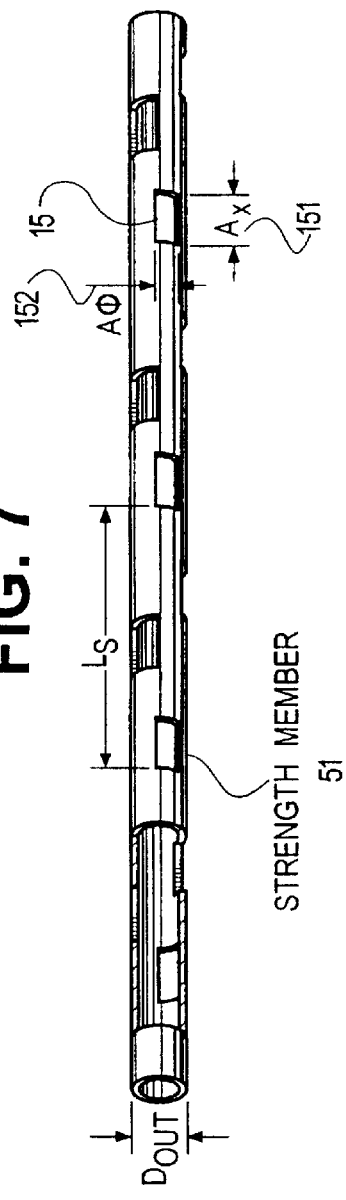
FIG. 7 is a schematic depiction of the optical fiber of the invention with a strength member.

In yet another preferred embodiment of the device of the invention as illustrated in FIG. 7, a strength member may be optionally added. This strength member is very thin, and even with the strength member, it is contemplated that the device of the invention is still less than 1 mm in diameter.

Figure 9:
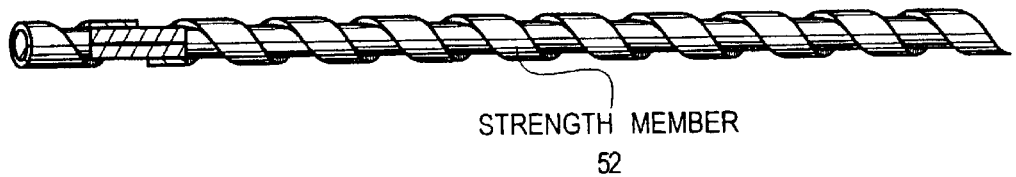
FIG. 9 is a schematic depiction of a catheter of the invention provided with a spiral strength member.

To preserve the omnidirectional scanning ability of the invention, the optical fiber is placed into the strength member 51 comprising a plurality of rectangular apertures 15. These apertures 15 have a length dimension 151 along axis $x=A_x$, and a circumferential dimension length $152=A_{\phi0}152$. In a preferred embodiment the apertures are rectangular, although other shapes may be utilized. The apertures 15 may be distributed throughout the imaging portion of the device, and may be distributed in a pattern, for example a spiral as illustrated in FIG. 9.

EXAMPLE 6

Figure 8:
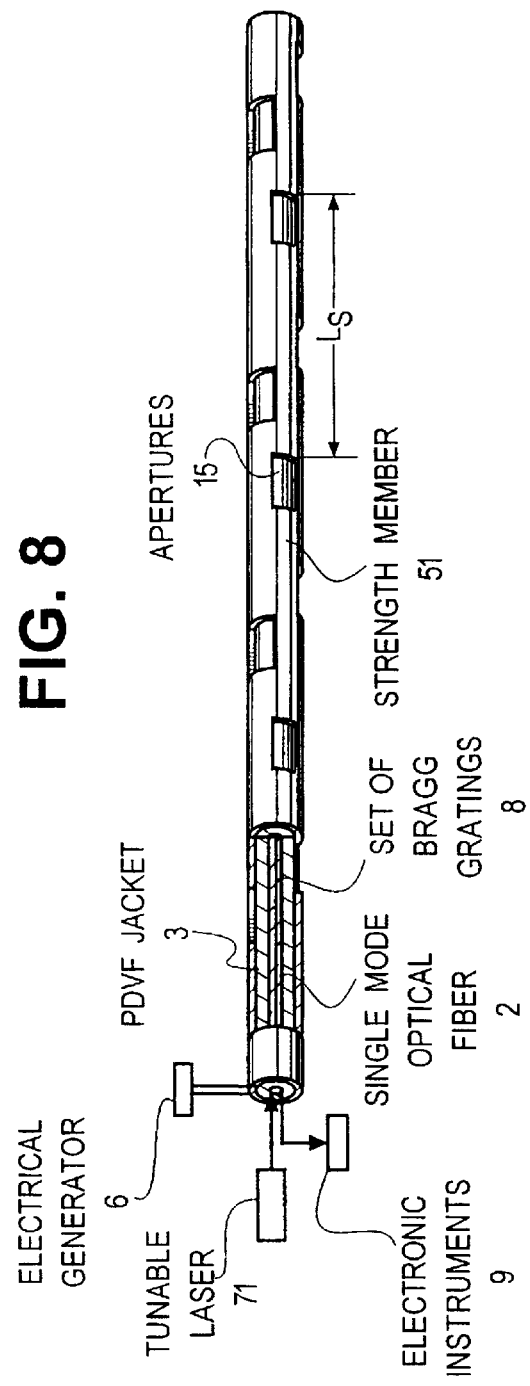
FIG. 8 is a schematic depiction of an ultrasound imaging catheter of the invention.

Example 6, as illustrated in FIG. 8, is a catheter version of the device of the invention, which produces ultrasound scanning both along the axis and along the circumference. It is comprised of a single mode optical fiber 2 with a plurality of Bragg gratings 8. The optical fiber is provided with a jacket 3, and a strength member 51, which has set of apertures 15. The strength member may be made of any hard, flexible and durable biocompatible material such as metal. Apertures are placed uniformly on the surface of strength member, both along the length and angle. The outside diameter of this device is less than 1 mm, and most preferably less than 0.5 mm. It is contemplated that the device may further have a most preferred outer diameter of less than $400\mu$. The apertures may be constructed using conventional photochemistry technology.

As illustrated in FIG. 8, the device is shown with an array of apertures $A_x=A_{\phi0}=200\mu$, period $L_S=1000\mu$. By applying electrical impulses to the electrodes of PVDF jacket 3 from electrical generator 6 we generate acoustical impulses in the all apertures simultaneously. The ultrasound impulses will expand in a direction perpendicular to the optical fiber surface, and reflect back from the nonhomogeneous medium (tissue). By tuning the laser 71, it is possible to realize scanning of the received ultrasound signals. Electronic instruments 9 receive, process and displaying the resulting images. One can estimate the scanning period $L_S$ of scanning as 0.5 to 1.0 mm lengthwise and number of directions around the fiber as 5 to 10.

EXAMPLE 7

The design of the invention may also comprise more than one optical fiber. If there are a plurality of fibers within the strength member, it is possible to decrease the period and increase the number of directions of the scanning.

EXAMPLE 8

FIG. 9 shows a variation of the strength member 52, comprising a spiral strength member. Use of this member is believed to produce smoother scanning, and a simpler manufacture than a strength member with apertures.

EXAMPLE 9

Figure 10:
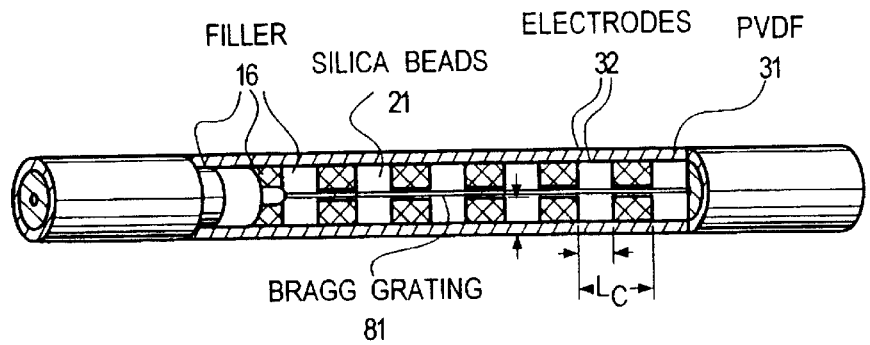
FIG. 10 is a schematic depiction of a fiber with bead-shaped cladding.

As illustrated in FIG. 10, another variation of the device of the invention is a variable diameter cladding, preferably of silica, with a period L along the fiber. This variation is achieved by the use of beads 21, which causes an increased sensitivity to acoustical waves. Maximum efficiency is achieved if the period $L_c$ is equal to one of the following resonance lengths: it is approximately equal to acoustical wavelength in water $L_{c1}$ Å $(1500/40 \cdot 10^6)=37.5 \cdot 10^{-6}$ m (for 40 MHz); or it is equal to the quasi-Lamb wavelength in the silica fiber $L_{c2}$.

In this embodiment, the Bragg grating interacts with optical waves and with the acoustical grating formed by the beads.

EXAMPLE 10

As illustrated in FIG. 10, an additional increase in sensitivity f the device may optionally be received if a filler 16 is used to fill the gaps between the beads. This filler is produced from material with comparatively low acoustical impedance, such as a solid polymer, gel, fluid or other suitable material. For the purpose of yet additional increasing in sensitivity, gap filling filler is selected from the materials which sound velocity $c_f$ lower than sound velocity in water (blood), that is $c_f<1500$ m/sec. One example of such materials is silicon rubber having the sound velocity $c_f\sim1000$ m/sec. In consequence of the sound velocity difference the energy focusing is achieving. Thus, the filling material functions as a signal collecting lens.

EXAMPLE 11

Figure 11:
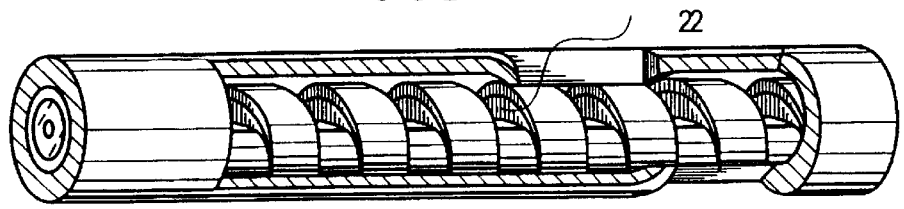
FIG. 11 is a schematic depiction of a fiber of the invention with bead cladding and with a spiral strength member.

Yet another variation of the device of the invention includes a spiral jacket 22, as shown in FIG. 11.

EXAMPLE 12

Figure 12:
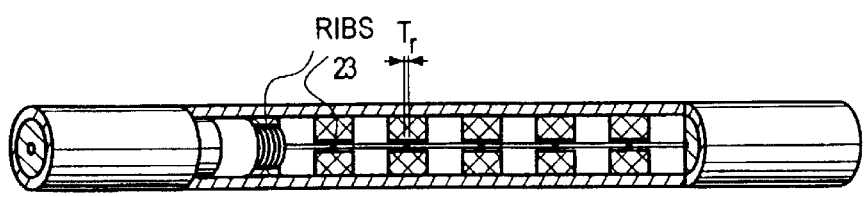
FIG. 12 is a device of the invention with bead cladding and with ribs.

Another embodiment (illustrated in FIG. 12) includes adding ribs 23 to the jacket In one example of a device with ribs, to achieve 40 MHz resonance, silica ribs should nave approximately dimensions: height $H_r$ 32 10 microns and thickness $T_r=4.5$ microns. The oscillations of ribs 23 induce the additional deformations at the fiber axes, hence causing the increasing in sensitivity. It is possible to fabricate ribs by conventionally known micromachining technology.

In a deviation of the ribbed embodiment, the ribs may have varying thicknesses, which are believed to lead to acoustical damping, and hence an increase in bandwith and resolution. If each of the ribs 23 will have different height $H_r$ and width $T_r$ then they will resonate at different frequencies.

EXAMPLE 13

Figure 13:
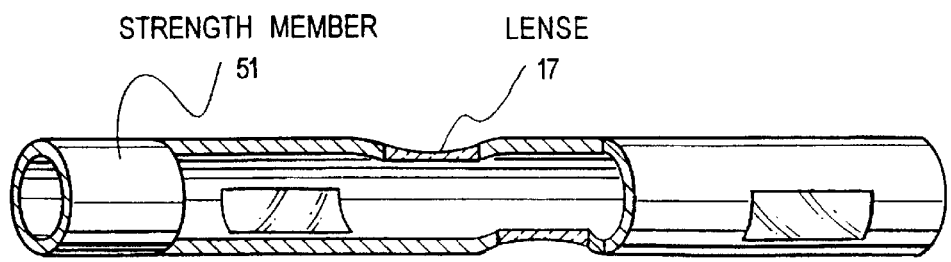
FIG. 13 is a catheter of the invention adapted with lens apertures.

For the purpose of yet additional increases in sensitivity, the apertures of the strength member may filled with a material with a velocity $c_L>1500$ m/sec, and an outside surface curvature which forms a focused lens, as illustrated in FIG. 13.

It is thus seen from the above description of the preferred embodiments that the objects of the invention are attained. Variations on this embodiment will be apparent to those skilled in the art without departing from the scope of the invention. All matter contained in the above description and the accompanying drawings is intended to be illustrative of the invention, and not limiting in the scope of the invention.

What is claimed is:

1. A device for imaging of an object, primarily for vascular imaging, the device comprising:

an optical fiber provided with a core, the core having an intracore written Bragg grating, the fiber being capable of reflecting light after illuminating thereof by a turnable laser beam, the reflected light is defined by a wavelength having a period corresponding to that of the Bragg grating;

a jacket at least partly surrounding the optical fiber, the jacket comprising a piezoelectric transducer for emanating omnidirectionally ultrasonic waves in response to an alternating voltage applied thereto, the ultrasonic waves after being reflected by the object being capable of inducing deformations within the core accompanied by modulation of the reflected light which can be detected and used for creation an image, and a tubular strengthening member surrounding the jacket, the member being provided with at least one aperture located in a relationship with respect to the Bragg grating so as to pass the ultrasonic waves reflected by the ultrasonic waves therethrough.

2. A device for imaging as defined in claim 1 in which the Bragg grating is written continuously along the core and the period of the Bragg grating continuously varies.

3. A device for imaging as defined in claim 1 in which the Bragg grating is written in discrete separate locations of the core.

4. A device for imaging as defined in claim 3 in which the period of the Bragg grating is kept constant along the same discrete location and varies from one discrete location to another discrete location.

5. A device for imaging as defined in claim 1 in which the aperture is configured as a square defined by a longitudinal dimension A and by a circumferential dimension.

6. A device for imaging as defined in claim 1 in which the strengthening member is provided with plurality of apertures, the apertures reside opposite to the discrete locations of the core so as to overlap therewith.

7. A device for imaging as defined in claim 6 in which the apertures are distributed along the strengthening member so as to reside on at least one cylindrical helix.

8. A device for imaging as defined in claim 1 in which the thickness of the jacket is chosen so as to achieve resonant response when the frequency of the ultrasonic waves lies in the range 20–150 mHz.

9. A device for imaging as defined in claim 8 in which the thickness of the jacket is at least 10 microns.

10. A device for imaging as defined in claim 1 in which the fiber is provided with plurality of annular recesses made in the fiber's periphery, the recesses are separated by a constant distance L the recesses are filled with a polymeric material in which velocity of sound propagation C<1500 m/sec.

11. A device for imaging as defined in claim 10 in which the polymeric material is silicon rubber.

12. A device for imaging as defined in claim 10 in which bottoms of the recesses are provided with ribs, the ribs being defined by a height dimension H and by a thickness dimension T.

13. A device for imaging as defined in claim 12 in which at least part of the apertures is plugged by a material in which velocity of sound propagation C<1500 m/sec.

14. A device for imaging as defined in claim 13 in which the outwardly facing surface of the material is configured to imitate focused lens.

15. A device for imaging as defined in claim 14, in which the outwardly facing surface is concave.

16. A device for imaging as defined in claim 1 in which the aperture is configured as a spiral window continuously extending along the strengthening member.

* * * * *

UNITED STATES PATENT AND TRADEMARK OFFICE
CERTIFICATE OF CORRECTION

PATENT NO. : 6,659,957 B1
DATED : December 9, 2003
INVENTOR(S) : Vardi et al.

It is certified that error appears in the above-identified patent and that said Letters Patent is hereby corrected as shown below:

Title page,
Item [56], References Cited, U.S. PATENT DOCUMENTS, after "O'Donnell" insert -- et al. --.
OTHER PUBLICATIONS, "Davis, M.A., et al.", reference, delete "IEE" and insert -- IEEE --, therefor; "Furstenau, N., et al.," reference, delete "IEE" and insert -- IEEE --, therefor.; "Lockey,R.A.,", reference, insert -- et. al., -- before "Multicomponent".
"Lockey,R.A.," reference, delete "IEE" and insert -- IEEE --, therefor; "Macpherson, W. N., et al.," reference, delete "IEE" and insert -- IEEE --, therefor; "McCulloch, S., et al.," reference , delete "IEE" and insert -- IEEE --, therefor; "Yoshino, T., et al.," reference, delete "IEE" and insert -- IEEE --, therefor; and ; "Yoshino, T., et al.," reference, delete "IEE" and insert -- IEEE --, therefor.
Item [57], ABSTRACT,
Line 6, delete "piezo-ceramic" and insert -- piezoceramic --, therefor.

Column 1,
Line 50, delete "films" and insert -- film --, therefor.
Line 60, delete "then" and insert -- than --, therefor.
Line 62, delete "ration" and insert -- realation --, therefor.

Column 2,
Line 15, delete "mm.," and insert -- mm, --, therefor.
Line 20, delete "that" and insert -- than --, therefor.
Line 39, delete "enables" and isnert -- enable --, therefor.

Column 3,
Line 29, delete "is" before "optical".
Line 46, delete "the" and isnert -- The --, therefor.

Column 6,
Line 32, delete "achieving" and insert -- acheived --, therefor.
Line 42, after "jacket" insert -- . --.
Line 43, delete "nave" and insert -- have --, therefor.
Line 44, delete "approximately" and insert -- approximate --, therefor and delete "$H_r$ 32 10" and insert -- $H_r = 10$ --, therefor.
Line 57, after "may" insert -- be --.

Column 7,
Line 6, delete "turnable" and insert -- tunable --, therefor .
Line 17, after "creation" insert -- of --.
Line 22, after "the" insert -- object --.
Line 22, delete "ultasonic waves" before "therethrough"

UNITED STATES PATENT AND TRADEMARK OFFICE
CERTIFICATE OF CORRECTION

PATENT NO. : 6,659,957 B1
DATED : December 9, 2003
INVENTOR(S) : Vardi et al.

It is certified that error appears in the above-identified patent and that said Letters Patent is hereby corrected as shown below:

Column 8,
Line 10, delete "mHz" and isnert -- MHz --, therefor.
Line 16, after "L" insert -- , --.

Signed and Sealed this

Seventeenth Day of August, 2004

JON W. DUDAS
*Acting Director of the United States Patent and Trademark Office*